United States Patent [19]

Wurschum et al.

[11] Patent Number: 5,271,897
[45] Date of Patent: Dec. 21, 1993

[54] DEVICE FOR RAISING AND LOWERING COVERS OF CONTAINERS FILLED WITH LIQUID TO BE ANALYZED

[75] Inventors: Hans P. Wurschum, Ostfildern; Walter Heissler, Wendlingen, both of Fed. Rep. of Germany

[73] Assignee: Eastman Kodak Company, Rochester, N.Y.

[21] Appl. No.: 913,551

[22] Filed: Jul. 14, 1992

[30] Foreign Application Priority Data

Jul. 16, 1991 [DE] Fed. Rep. of Germany ....... 4123528

[51] Int. Cl.⁵ .............................................. G01N 35/00
[52] U.S. Cl. ........................................ 422/63; 422/65; 422/100
[58] Field of Search ........................... 422/63, 65, 100

[56] References Cited

U.S. PATENT DOCUMENTS

| | | |
|---|---|---|
| 1,842,210 | 1/1932 | Scruton . |
| 3,098,721 | 7/1963 | Jewell ................................. 23/259 |
| 3,753,657 | 8/1973 | Downing et al. .................. 422/65 |
| 3,993,452 | 11/1976 | Moulding .......................... 23/259 |
| 4,343,766 | 8/1982 | Sisti et al. ........................ 422/100 |
| 4,347,215 | 8/1982 | Sisti et al. ........................ 422/100 |
| 4,455,280 | 6/1984 | Shinohara et al. ................. 422/63 |
| 4,515,286 | 5/1985 | Ushikubo ......................... 220/314 |
| 4,824,641 | 4/1989 | Williams ............................ 422/63 |
| 4,883,189 | 11/1989 | Lobbert ............................ 220/1 T |
| 5,008,082 | 4/1991 | Shaw ................................. 422/63 |

FOREIGN PATENT DOCUMENTS 3141780  5/1983  Fed. Rep. of Germany .

*Primary Examiner*—Jill A. Johnston
*Assistant Examiner*—Ramon Torres
*Attorney, Agent, or Firm*—Dana M. Schmidt

[57] ABSTRACT

A device for removing and re-applying a cover to an open container of a liquid aspirated in an analyzer, the device including a plurality of receptacles disposed in an array for holding a plurality of containers of a liquid, a cover for each of the receptacles of a size and shape sufficient to sealingly cover a container in each receptacle, a mechanism for permanently attaching the cover to the receptacle, the mechanism including a retainer of each of the covers that is pivotally mounted on the receptacle and a bi-stable pivot in the device for pivoting and holding the retainer and thus its cover in either a first position in which the cover contacts and closes a container, or a second position in which the cover is held raised away from contact with any container in the receptacle by means of a leaf spring pressed against a cam.

3 Claims, 2 Drawing Sheets

DEVICE FOR RAISING AND LOWERING COVERS OF CONTAINERS FILLED WITH LIQUID TO BE ANALYZED

FIELD OF THE INVENTION

The invention relates to a device comprising receptacles that hold containers of liquid that must be covered except when the liquid contents are being aspirated.

BACKGROUND OF THE INVENTION

In analyzers for testing biological fluids, for example the analyzer shown in U.S. Pat. No. 5,008,082, the patient's biological fluid is supplied via sample tubes to an aspirator, which then delivers it as is to a slide test element, or in some cases, to a dilution cup to which a diluent is added, also by the aspirator. Such diluents are supplied to the aspirator of the analyzer via vials or cups which are periodically refilled by the operator. However, it is important that such vials be re-capped or re-covered when aspiration is not occurring, to prevent evaporation. Covers which have to be removed and reapplied manually are unacceptable since they involve too much operator intervention.

It is known from the prior art to provide for automated means that remove covers of tubes of patient sample. See, for example, DE - GM 3,141,780. However, the covers that are removed are stoppers that are not replaced, so that such automated mechanism contributes nothing to automated means for removing and then replacing the covers of vials of liquid such as diluents. Still further, since the covers in question in the case of the stoppers of the prior art are not permanently mounted in the analyzer, they are potentially parts that can become loose within the analyzer, and therefore a source of jams.

Therefore, there has been a need prior to this invention to provide a device for automated removal and re-application of covers for containers in an analyzer, the covers being permanently secured to the device.

SUMMARY OF THE INVENTION

There is provided a device that meets the aforesaid need.

More specifically, there is provided a device for removing and re-applying a cover to an open container of liquid to be aspirated in an analyzer, the device comprising a plurality of receptacles disposed in an array for holding a plurality of containers of such liquid, a cover for each of the receptacles, of a size and shape sufficient to sealingly cover a container placed in each receptacle, means for permanently attaching the cover to the receptacle, the attaching means including a retainer of each of the covers that is pivotably mounted on the receptacle, and bi-stable pivot means in the device for pivoting the retainer and thus its cover towards and away from a container in the receptacle.

Accordingly, it is an advantageous feature of the invention that containers of diluent or other additive liquids are provided in an analyzer with covers that are both automatically operated for aspiration, and by their permanence do not become loose within the analyzer.

It is a related advantageous feature that the automatic operation of the covers permits manual operation as well.

Other advantageous features will become apparent upon reference to the following Detailed Description when read in light of the attached drawings, in which:

IN THE DRAWINGS

FIG. 1 shows a top view of the device according to the invention installed in the processing station of an analyzer; and FIG. 2 shows a lateral view of the device according to FIG. 1 (cross-section along a line II—II in FIG. 1).

DESCRIPTION OF THE PREFERRED EMBODIMENTS

What follows is a description as the invention is applied to the preferred embodiments, in which the liquid contained is a diluent. Additionally, the invention is useful for containers of any liquid that is added to the patient sample in an analyzer, for any purpose. Because the covers of the device are permanently attached, the device most preferably is not used to provide the biological fluid samples, which usually come with their own covers (e.g., stoppers) already in place.

Figure 1:
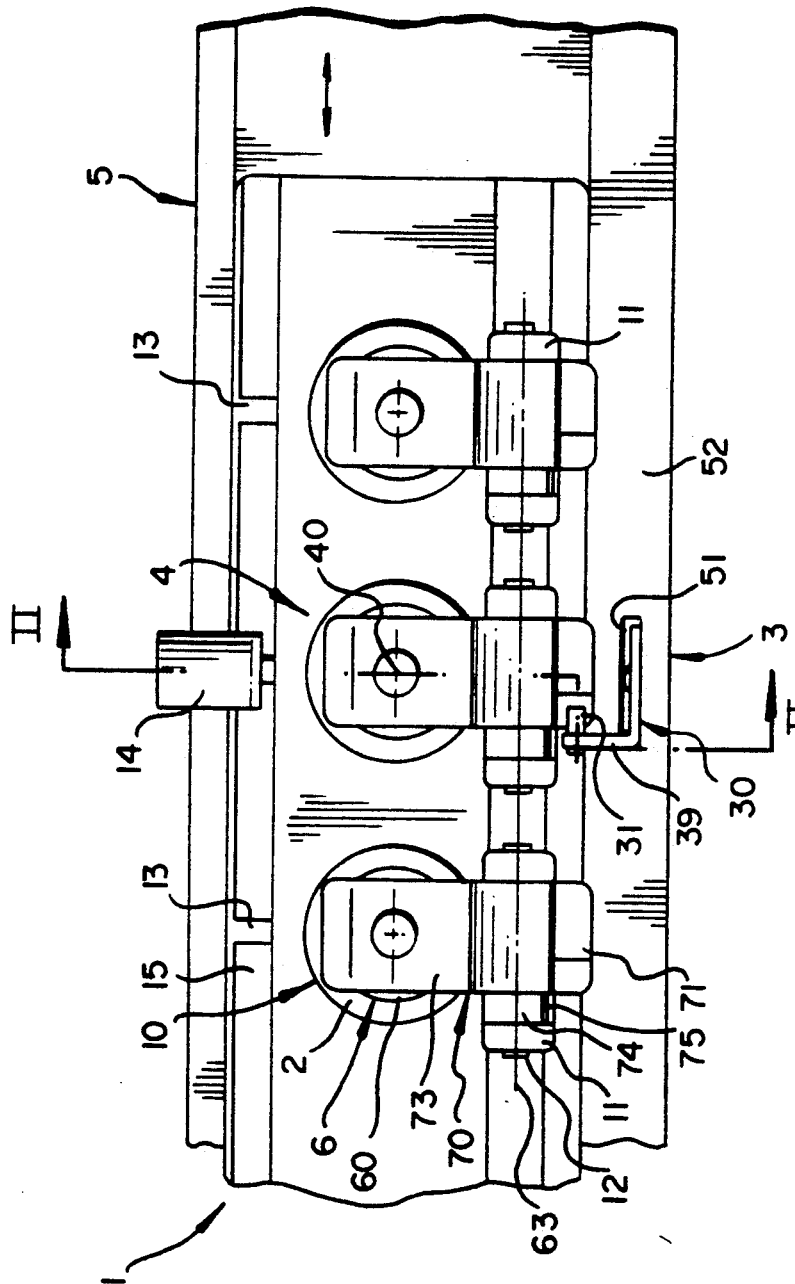

The device shown in FIG. 1 is arranged on a transport path 5 in the area of a processing station 4 of an analyzer.

Device 1 consists of a plurality of arranged receptacles 10 to receive containers 2 filled with liquid to use in the analysis. Preferably, receptacles 10 are linearly disposed.

Each receptacle 10 comprises a cover means 6 illustrated in its covering position and designed as a lid 60 arranged on an outrigger handle 73 of a retainer 70 and associated with the opening 20 of a container 2, said lid being pivotable about an axis of rotation 63 of a pin 12 extended along a longitudinal side of the device and supported in bearings 11 of a retainer.

On a longitudinal side of device 1 extending opposite to the bearings 11 each receptacle 10 is associated with a sensing mark 13 designed as a slot and arranged in a horizontally extending bar 15.

One of the receptacles 10 is aligned with an actuating means 3 arranged in processing station 4 and with an aspirating station 40 for the liquids of the containers 2 in which a sensor 14 designed as an optoelectric switch is arranged for detecting the sensing mark 13.

The actuating means 3 comprises an actuating element 30 including an actuating pin 31 projecting into the area of an arm 71 of retainer 70.

On one of its sides, retainer 70 includes a cam 74 which is concentrically arranged to the axis of rotation 63 and which is engaged by a hold-down element 75.

Figure 2:
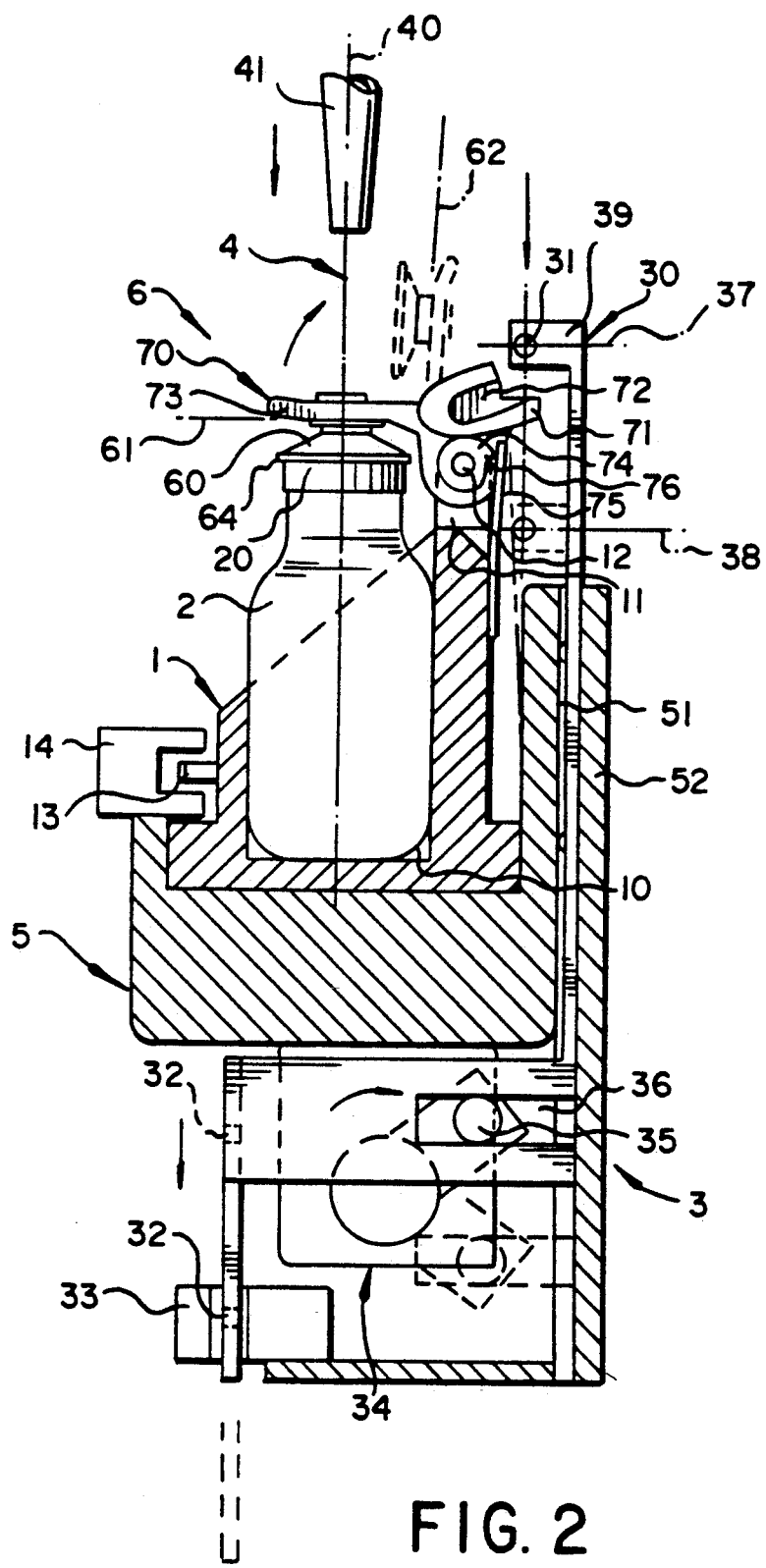

In FIG. 2, the lid 60 is shown both in its covering position 61 and in its uncovering position 62. Above the lid an aspirating head 41 is illustrated which is aligned with the center axis of container 2.

Beneath transport path 5 a microprocessor controlled, motor-driven eccentric drive 34 of actuating means 3 is arranged with its drive pin engaging with a horizontally protruding bifurcated lever arm 36 of actuating element 30.

Actuating element 30 which is designed as a flat slider is guided in a vertically extending channel 51 of a side wall 52 of transport path 5. In the area of the lower end of the actuating element 30 two sensing apertures 32 are arranged one above the other to cooperate with a sensor 33, said apertures being associated with the covering position 61 and the uncovering position 62 of the lid 60 or with the upper end position 37 and the lower end position 38 of the actuating element.

In its upper end position 37, an actuating pin 31 of actuating element 30 mounted to a retaining arm 39 is positioned above and outside a bifurcated guide means 72 of arm 71 of retainer 70, in which case the lid 2 lies planarly on the opening 20 of a container with the hold-down element 75 formed as a leaf spring engaging the extreme end of a flattened cam section 76 of cam 74.

In its lower end position 38, the actuating pin 31 rests on the lower prong of the fork of guide means 72, the lid 60 being positioned in a vertical uncovering position 62 pivoted by about 100 degrees from its previous position and the hold-down element 75 contacting the periphery of cam 74.

The device operates as follows: Initially, the device 1 is equipped with containers 2 filled with liquid outside the analyzer. For this purpose, the cover means 6 is manually pivoted by actuating retainer 70 by means of its outrigger handle 73 and moving it together with lid 60 from its horizontal covering position 61 to its vertical uncovering position 62. Then the closure (not illustrated) of a container 2 is removed and the container placed in the receptacle 10 of device 1. Subsequently, retainer 70 is manually pivoted back to its covering position 61 so that the opening 20 of the container is covered by the lid (see FIG. 2). This procedure is repeated until all receptacles 10 of device 1 are equipped with containers 2. In an input station (not illustrated) of the analyzer the device 1 is now placed on the horizontally extending transport path 5 and moved to a processing station 4 (shown in FIGS. 1 and 2) by means of a microprocessor-controlled transport means (not illustrated). In this position, device 1 is aligned with a receptacle 10 in the area of the actuating means 3 or with a container 2 in the aspirating station 40 beneath the aspirating head 41. Alignment is effected by means of sensor 14 arranged at the transport path 5 and the sensing marks 13 of device 1.

Then the actuating element 30 of the actuating means 3 is pulled down by means of the drive pin 35 of the microprocessor controlled, motor-driven eccentric drive 34. First, the lower sensing aperture 32 of the actuating element 30 is moved out of the sensing range of sensor 33. Then actuating pin 31 arranged at the upper end of the actuating element 30 hits the lower prong of guide means 72 of arm 71 and pivots retainer 70 together with lid 60 from its covering position 61 to its uncovering position 62. Actuating element 30 is moved downwards until it has reached the sensing range of sensor 33.

Then the aspirating head 41 is lowered into container 2 for removing liquid and, after an upward movement to its upper end position, moved to a further processing station (not illustrated).

Subsequently, eccentric drive 34 is started again and retainer 70 together with lid 60 is pivoted back to the covering position 61 by means of actuating element 30. Actuating pin 31 thereby hits first the upper prong of guide means 72 and pivots retainer 70 from its approximately vertical uncovering position 62 to its approximately horizontal covering position 61 before it releases guide means 72.

In this position, cam 74 of retainer 70 has pivoted about the axis of rotation 63 to the extent that cam section 76 contacts hold down element 75 and thus forms a lever arm which by means of the spring force of hold-down element 75 produces a torque that urges retainer 70 into its covering position 61 and presses lid 60 onto the opening 20 of container 2 such that evaporation, contamination or spilling of the liquid within and outside the analyzer is reliably prevented.

Thus, section 76 is a point of instability in cooperation with the spring action of element 75 such that the contact of element 75 against cam 74 urges the cam to rotate towards the first position contacting a container with the cover, when element 75 passes over section 76.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. In an analyzer including an aspirator and a device for removing and re-applying a cover to an open container of a liquid to be aspirated in an analyzer, said device comprising a plurality of receptacles disposed in an array for holding a plurality of containers of a liquid;

a cover for each of said receptacles, with a predetermined size and shape sufficient to sealingly cover a container placed in said each receptacle;

and means for permanently attaching each said cover to a respective one of said receptacles, said attaching means including a retainer for each of said covers that is pivotably mounted on said receptacle;

the improvement wherein said analyzer further includes bi-stable pivot means in said device for pivoting and holding each retainer and its cover in selective alternative positions, said bi-stable pivot means comprising a cam mounted to rotate with said each retainer and having an instability projection extending beyond the rest of said cam, and a leaf spring frictionally engaging said cam to hold said cover in a raised position and alternatively to bias against said projection when said retainer is rotated sufficiently to close a respective cover against a container;

and means for actuating said bi-stable pivot means.

2. A device as defined in claim 1, and further including sensing means for sensing when said retainer has uncovered a container, and means responsive to said sensing means to signal that a container is available in the device.

3. A device as defined in claim 1, and further including a manual handle attached to each retainer.

* * * * *